United States Patent
Schowalter et al.

(10) Patent No.: US 8,349,255 B2
(45) Date of Patent: Jan. 8, 2013

(54) TISSUE PROCESSING SYSTEM AND METHOD

(75) Inventors: Joseph P. Schowalter, South Lebanon, OH (US); Prasanna Malaviya, Mason, OH (US); David A. Witt, Maineville, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 244 days.

(21) Appl. No.: 12/777,723

(22) Filed: May 11, 2010

(65) Prior Publication Data

US 2011/0281350 A1 Nov. 17, 2011

(51) Int. Cl.
*G01N 21/00* (2006.01)
(52) U.S. Cl. ............ 422/65; 422/68.1; 422/50; 422/500; 422/536; 436/180
(58) Field of Classification Search .................. 241/236; 422/64–67, 68.1, 50, 500, 536; 436/180
See application file for complete search history.

(56) References Cited

U.S. PATENT DOCUMENTS

| | | | |
|---|---|---|---|
| 5,526,822 A | 6/1996 | Burbank et al. | |
| 5,694,951 A | 12/1997 | Bonutti | |
| 6,086,544 A | 7/2000 | Hibner et al. | |
| 6,990,982 B1 | 1/2006 | Bonutti | |
| 7,115,100 B2 | 10/2006 | McRury et al. | |
| 7,442,171 B2 | 10/2008 | Stephens et al. | |
| 7,611,473 B2 | 11/2009 | Boock et al. | |
| 2002/0074438 A1* | 6/2002 | Horigane | 241/236 |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2006/0074345 A1 | 4/2006 | Hibner | |
| 2007/0001045 A1 | 1/2007 | Aizenberg et al. | |
| 2008/0071385 A1 | 3/2008 | Binette et al. | |
| 2008/0214955 A1 | 9/2008 | Speeg et al. | |
| 2008/0234715 A1 | 9/2008 | Pesce et al. | |
| 2008/0311219 A1 | 12/2008 | Gosiewska et al. | |
| 2010/0160819 A1 | 6/2010 | Parihar et al. | |

FOREIGN PATENT DOCUMENTS

EP 1 908 524 4/2008

OTHER PUBLICATIONS

International Search Report dated Sep. 1, 2011 for Application No. PCT/US2011/035914.
U.S. Appl. No. 12/483,305, filed Jun. 12, 2009, Hibner et al.

* cited by examiner

*Primary Examiner* — Jyoti Nagpaul
(74) *Attorney, Agent, or Firm* — Frost Brown Todd LLC

(57) ABSTRACT

A tissue processing system includes a tray and a processing component. The processing component has teeth configured to dice, mince, and mix the tissue in the tray. In some versions, teeth of a rotary member mesh with teeth of a stationary member, such that the tissue is ground between the meshing teeth. The rotary member may be moved in an orbital path relative to the stationary member. In some versions, the teeth of two rotary members mesh together, and the rotary members are rotated in opposite directions to grind the tissue. The rotary members may also be alternatingly moved up and down to perform initial dicing on the tissue. Once the tissue has been processed, the tissue may then be used in a therapeutic manner, such as by being incorporated with a scaffold and then implanted in the same patient from whom the tissue was originally harvested.

7 Claims, 12 Drawing Sheets

TISSUE PROCESSING SYSTEM AND METHOD

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, now U.S. Pat. No. 7,794,408, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
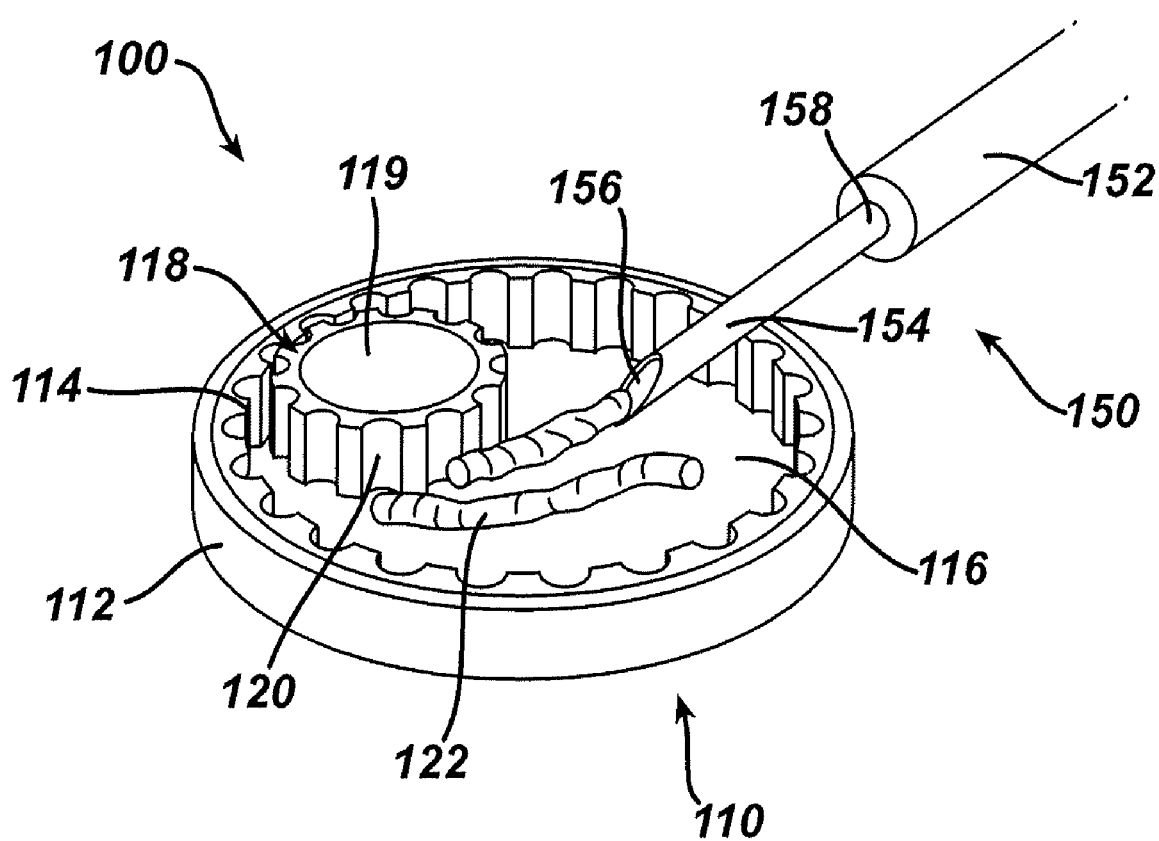
FIG. 1 is a perspective view of an exemplary version of a tissue processing system, showing tissue being deposited into the system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly(amino acid), agarose, amylose, hyaluronan, polyhydroxybutyrate (PHB), hyaluronic acid, poly(vinyl pyrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, now U.S. Pat. No. 7,442,171; U.S. Pub. No. 2008/0214955, entitled "Presentation of Biopsy Sample by Biopsy Device," published Sep. 4, 2008; U.S. Non-Provisional Pat. App. No. 12/337,942, entitled "Biopsy Device with Central Thumbwheel," filed Dec. 18, 2008, published as U.S. Pat. Pub. No. 2010/0160819; and U.S. Non-Provisional Pat. App. No. 12/483,305, entitled "Tetherless Biopsy Device with Reusable Portion," filed Jun. 12, 2009, now U.S. Pat. No. 8,206,316. The disclosure of each of the above-cited U.S.

Patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 $mm^3$ and approximately 2 $mm^3$; or more particularly between approximately 0.05 $mm^3$ and approximately 1 $mm^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc.). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Devices for Processing Tissue

As described above, some medical treatments and procedures may include the processing of tissue. Such processing of tissue might generally involve the steps of dicing, mincing, or mixing tissue. Any one of the steps of dicing, mincing, or mixing may be performed without the other steps or the steps may be performed in combination with one another. It will also be appreciated that the user may desire to form processed tissue into a particular shape suited for a particular use. Several versions of the systems and methods described below may be used to perform some or all of these tasks so as to prepare the tissue for a desired application. Furthermore, components of the systems and methods described below may be interchangeable or substituted with components from alternative versions as will be apparent to one of ordinary skill in the art. Such substitutions and interchangeability may be performed without departing from the overall scope of the systems and methods described herein.

A. Exemplary Tissue Processing Device with Manual Grinder

Figure 2:
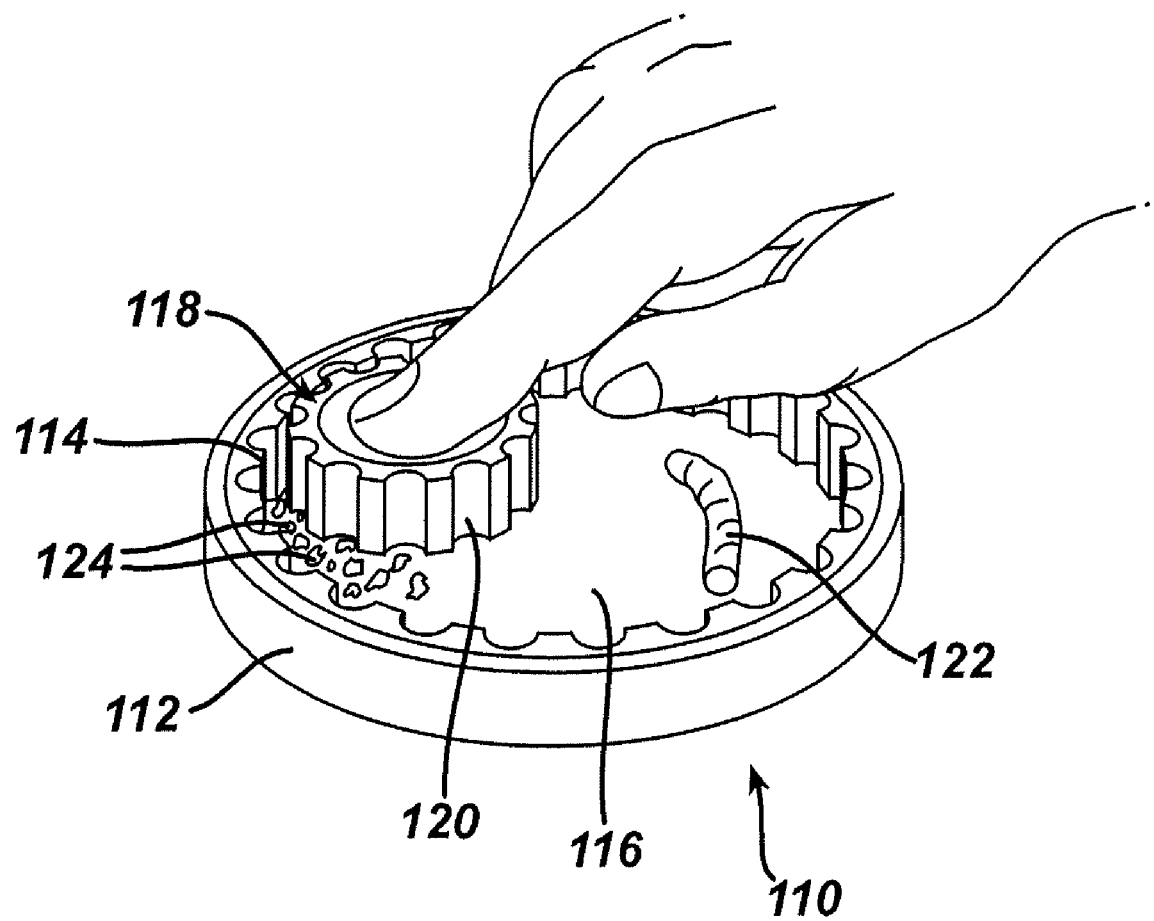
FIG. 2 is another perspective view of the tissue processing system of FIG. 1, showing the deposited tissue being ground by the system.
Figure 3:
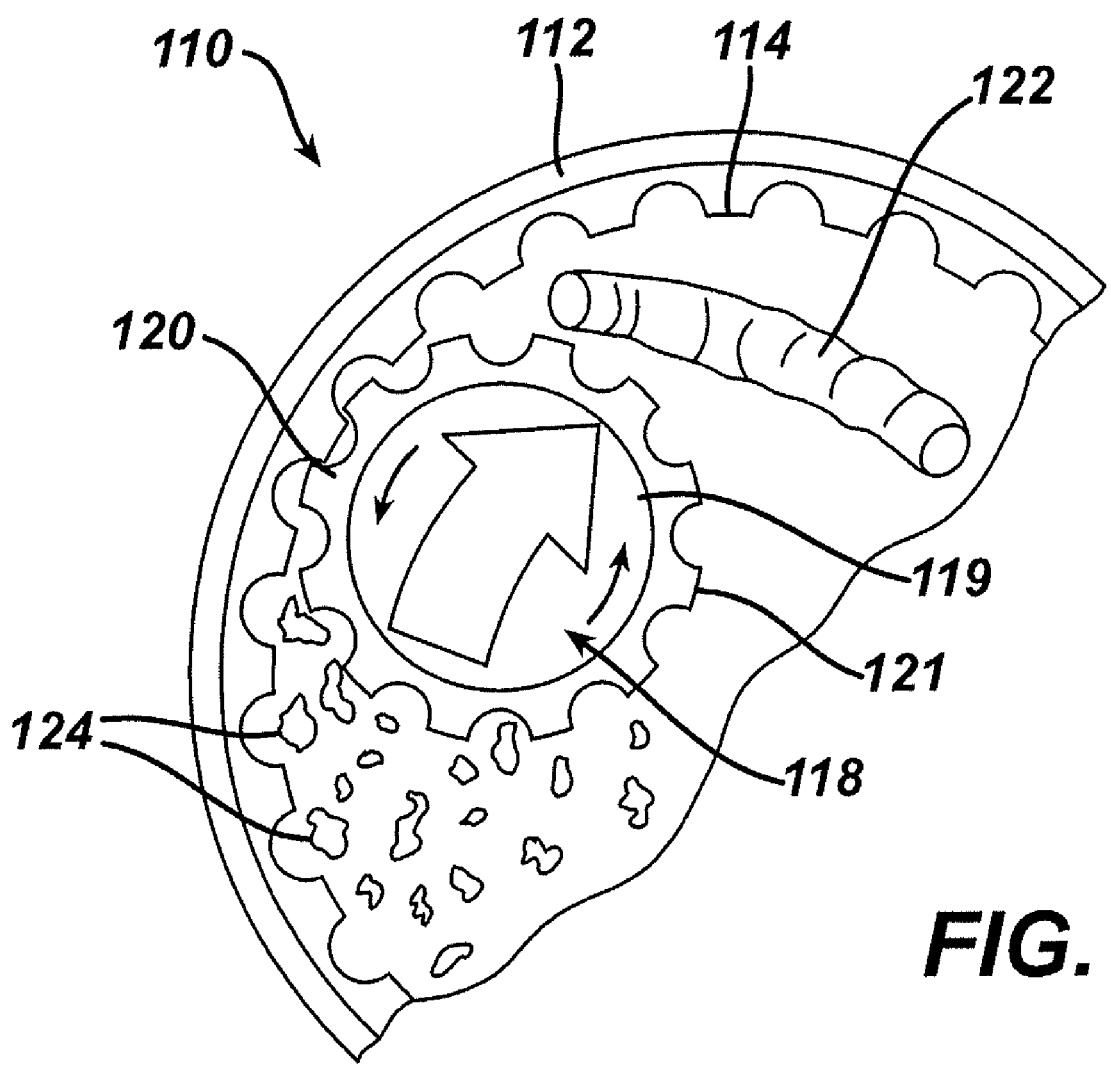
FIG. 3 is a partial top plan view of the tissue processing system of FIG. 1, showing the deposited tissue being ground by the system.

Turning now to FIGS. 1-3, FIG. 1 depicts an exemplary version of a tissue processing system (100). Tissue processing system (100) of this example comprises a tissue dispenser (150), a tissue processing tray (110), and a tissue grinder (118). As will be described in greater detail below, tissue processing system (100) is operable to process tissue cores (122) by grinding the tissue cores (122) into minced tissue (124). This minced tissue (124) may then be incorporated into a fibrin matrix or scaffold, or into a variety of other types of mixtures with any one or more medical fluid components as referred to herein, in accordance with the teachings of any of the patents or patent publications cited herein, or in any other suitable fashion. The resulting matrix, scaffold, or other type of mixture may then be administered to a patient (e.g., the person from whom tissue cores (122) were originally obtained, etc.) for therapeutic purposes and/or for other purposes, in accordance with the teachings of any of the patents or patent publications cited herein, or in any other suitable fashion.

Tissue dispenser (150) is operable to obtain one or more tissue cores (122) from a patient and deposit such tissue cores (122) in tissue processing tray (110). Tissue dispenser (150) of the present example comprises a tissue reservoir (152) and a tissue coring needle (154). Tissue dispenser (150) further comprises a pump feature such as a plunger (not shown), which may be used to urge a tissue core (122) out of tissue dispenser (150) through needle (154). Tissue reservoir (152) comprises a generally cylindrical chamber configured to hold tissue and/or other biological material(s) therein. However, any suitable shape for tissue reservoir (152) may be used. Tissue reservoir (152) may be constructed of a plastic, metal, or any other suitable material or combination of materials. Tissue reservoir (152) is in fluid communication with needle (154). However, tissue reservoir (152) may be configured to be in fluid communication with needle (154) on a selective basis. For example, needle (154) and/or reservoir (152) may have a switch, valve, or other suitable actuation feature to enable a user to separate material held in tissue reservoir (152) from needle (154). The actuation feature may then be engaged to permit tissue reservoir (152) and needle (154) to be in fluid communication.

Needle (154) is configured has a first end (158) and a second end (156). First end (158) connects to tissue reservoir (152) and second end (156) defines an opening through which tissue core (122) may be ejected from needle (154). Second end (156) comprises a generally cylindrical opening. However, any suitable shape for the opening may be used. For example, the opening of second end (156) may be a slotted opening, a serrated opening, or any other suitable variation. Needle (154) may be formed of stainless steel material, plastic, and/or any other suitable material(s). Of course, tissue dispenser (150) may take a variety of other forms. For instance, tissue dispenser (150) may alternatively be configured similar to a conventional biopsy device having a needle with a closed distal end and a side aperture, with a cutter being movably positioned within the needle to sever tissue protruding through the side aperture. Other suitable forms that a tissue dispenser (150) may take will be apparent to those of ordinary skill in the art in view of the teachings herein. In the present example, tissue dispenser (150) obtains tissue cores (122) from a patient's thigh muscle, though it should be understood that tissue cores (122) may come from any other suitable source. Furthermore, it should be understood that the same device that obtains tissue cores (122) need not necessarily be the same device that deposits tissue cores (122) in tissue processing tray (110).

Tissue processing tray (110) of the present example comprises a tray base (116) and tray wall (112). Tray base (116) and tray wall (112) of the present example are formed of a single piece of material, though it should be understood that tray base (116) and tray wall (112) may alternatively be constructed separately and later connected by glue, welding, screws, fasteners, or any other suitable means. Tray base (116) of the present example is generally circular in shape, though it should be understood that tray base (116) may alternatively be any other suitable shape, such as rectangular, triangular, ovular, elliptical, etc. Tray base (116) is generally flat and is further configured to receive tissue core (122) therein. Tray base (116) may comprise a non-stick material (e.g., a coating of polytetrafluoroethylene (PTFE), etc.); and/or may comprise a non-slip surface operable to prevent tissue core (122) from excessively sliding about tray base (116). Tray base (116) is large enough to hold tissue grinder (118) and tissue core (122), while providing enough room to allow tissue grinder (118) to move about tissue processing tray (110). In some other versions, tray base (116) has a radius that is only slightly larger than radius of tissue grinder (118) or any other suitable size as will be apparent to those of ordinary skill in the art in view of the teachings herein.

Tray wall (112) has a height sufficiently high so as to prevent tissue core (122) from escaping tissue processing tray (110) as tissue core (122) is being processed as will be described in further detail below. Tray wall (112) includes wall teeth (114) encircling at least a portion of the interior circumference of tray wall (112). In the present example, wall teeth (114) extend about the entire interior circumference of tray wall (112). Wall teeth (114) are further configured to complement and mesh with tissue interface wall (120) of tissue grinder (118) as will be discussed in more detail below. Tray wall (112) may comprise a generally non-stick material (e.g., a coating of polytetrafluoroethylene (PTFE), etc.) that is configured to provide a surface for processing tissue core (122). Wall teeth (114) generally comprise a series of rectangular protrusions extending around tray wall (112), separated by radially extending recesses. However, any other suitable shape or shapes for wall teeth (114) may be used.

Tissue grinder (118) of the present example comprises an outer tissue interface wall (120). Tissue grinder (118) has a generally circular, gear-like shape. However, any other suitable shape or shapes may be used. Tissue interface wall (120) has a series of rectangular protrusions (121) extending radially outwardly about the circumference of tissue grinder (118). Protrusions (121) complement and mesh with wall teeth (114) of tray wall (112). Top of tissue grinder (118) forms a recess (119) that is configured to receive a user's fingertip to operate tissue grinder (118) as shown in FIG. 2 wherein a user places his or her finger on the top of tissue grinder (118). A textured or grip surface may be provided by tissue grinder (118) within or in lieu of recess (119). Due to the meshing of teeth (114) and protrusions (119), tissue interface wall (120) and wall teeth (114) are configured to cooperate to mince or dice tissue core (122). Tissue grinder (118) is configured to move about the circumference of tissue processing tray (110) by serially engaging and disengaging wall teeth (114) in a generally circular motion. As shown in FIG. 3, as tissue grinder (118) is moved clockwise in an orbital fashion within tissue processing tray (110), tissue grinder (118) rotates counterclockwise. Tissue grinder (118) and tissue processing tray (110) thus together form a planetary gear system, with tissue processing tray (110) serving as a ring gear and with tissue grinder (118) serving as a planet gear. As teeth (114) and protrusions (119) mesh during this orbit and rotation, the area in which wall teeth (114) and protrusions (119) mesh is operable to mince or dice tissue core (122) or any other biological material.

In an exemplary use of tissue processing system (100), tissue core (122) is initially obtained from a patient using needle (154) of tissue dispenser (150). Tissue core (122) is then added to tissue processing tray (110) as shown in FIG. 1. Tissue core (122) is added by using tissue dispenser (150) with tissue core (122) contained in tissue reservoir (152). The user may actuate a pump feature (not shown) so as to urge tissue core (122) out of tissue dispenser (150) through needle (154). Needle (154) dispenses tissue core (122) onto the surface of tray base (116). After a sufficient amount of tissue core (122) has been added to tissue processing tray (110), the user engages tissue grinder (118) as shown in FIG. 2 and rotates tissue grinder (118) about the perimeter of tissue processing tray (110). As tissue grinder (118) moves about tissue processing tray (110), tissue interface wall (120) and wall teeth (114) continually engage and disengage with each other. As the position of tissue core (122) on tray base (116) intersects with the movement path of tissue grinder (118), and as tissue core (122) enters the area where tissue interface wall (120) and wall teeth (114) interface, tissue core (122) becomes processed by dicing, mincing, and/or mixing as shown in FIG. 3. The user may move tissue grinder (118) about tissue processing tray (110) in circular motions several times whereby each successive motion further processes tissue core (122), causing tissue core (122) to become further diced, minced, and/or mixed.

After tissue core (122) is sufficiently diced, minced, and/or mixed, the resulting minced tissue (124) may then be removed from tissue processing tray (110) in any suitable fashion, then subsequently processed and/or re-administered to the patient in accordance with the teachings herein and/or in accordance with the teachings in any patents and/or published patent applications cited herein. Of course, several tissue cores (122) may be introduced to tissue processing tray (110), serially and/or simultaneously, to produce a desired amount of minced tissue (124). To remove minced tissue (124) from processing tray (110), a user may simply lift and remove tissue grinder (118) from processing tray (110) and then scoop minced tissue (124) from processing tray (110). Of course, any suitable technique may be used to remove minced tissue (124) from processing tray (110).

In some other versions, tissue interface wall (120) may be constructed of a rotatable circular region that is separately rotatable from the center of tissue grinder (118), such that the user may push tissue grinder (118) about the perimeter of tissue processing tray (110) without having to reorient the user's finger as a result of an orbital motion of tissue grinder (118). In addition or in the alternative, tissue grinder (118) may be configured to connect to tray base (116) about a circular track (not shown) that extends about the perimeter of tray base (116) thus preventing tissue grinder (118) from sliding around portions of tray base (116), such that at least a portion of tissue grinder (118) is continually engaging tray wall (112). It should also be understood that tissue processing system (100) may include a plurality of tissue grinders (118) that orbit within tissue processing tray (110). Such tissue grinders (118) may be linked together such that they orbit and rotate simultaneously; or they may be independent of each other. Other suitable variations of tissue processing tray (110) and/or tissue grinder (118), as well as other suitable relationships between tissue processing tray (110) and tissue grinder (118), will be apparent to those of ordinary skill in the art in view of the teachings herein.

In still other versions, a crank shaft and/or other suitable mechanical actuator may be used to cause movement of tissue grinder (118) about the perimeter of tissue processing tray (110). In addition or in the alternative, an electronically controlled device may be used to cause the motion of tissue grinder (118) about the perimeter of tissue processing tray (110). As yet another merely illustrative variation, tissue processing system (100) may be configured such that tissue grinder (118) may be moved about the perimeter of tissue processing tray (110) in one direction (e.g., clockwise) to dice tissue core (122); and such that moving tissue grinder (118) may be moved about the perimeter of tissue processing tray (110) in a different direction (e.g., counterclockwise) to mince tissue core (122). Of course, tissue processing system (100) may also be configured such that movement of tissue grinder (118) about the perimeter of tissue processing tray (110) in one direction (e.g., clockwise) will both dice and mince tissue core (122) thereby producing a diced and minced tissue (124). In some such versions, tissue grinder (118) may be moved about perimeter of tissue processing tray (110) in a different direction (e.g., counterclockwise) to mix diced and minced tissue (124). It should also be understood that, during the process of dicing and mincing in various versions of tissue processing system (100), tissue core (122) and/or minced tissue (124) may become mixed; and furthermore, that a user may add other suitable materials (e.g., fibrin, polymer, etc.) to tissue processing tray (110) to be diced, minced, and/or mixed with tissue core (122) and/or minced tissue (124). Still other suitable features, components, configurations, functionalities, and operabilities that may be provided by tissue processing system (100) will be apparent to those of ordinary skill in the art in view of the teachings herein. Similarly, various other suitable ways in which tissue processing system (100) may be used will be apparent to those of ordinary skill in the art in view of the teachings herein.

B. Exemplary Tissue Processing Device with Dual Rotary Grinders

Figure 4:
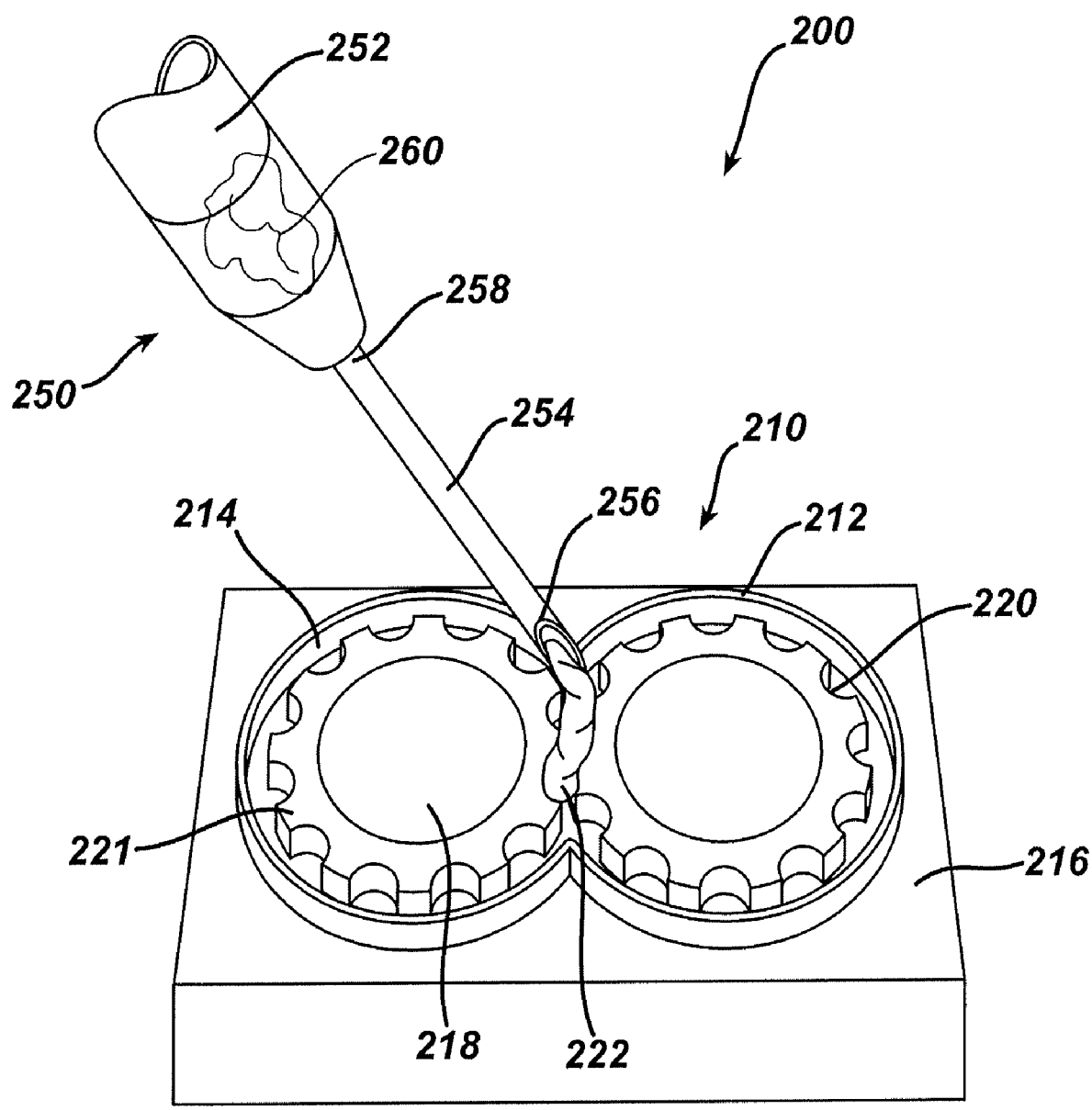
FIG. 4 is a perspective view of an exemplary alternative version of a tissue processing system, showing tissue being deposited into the system.
Figure 5:
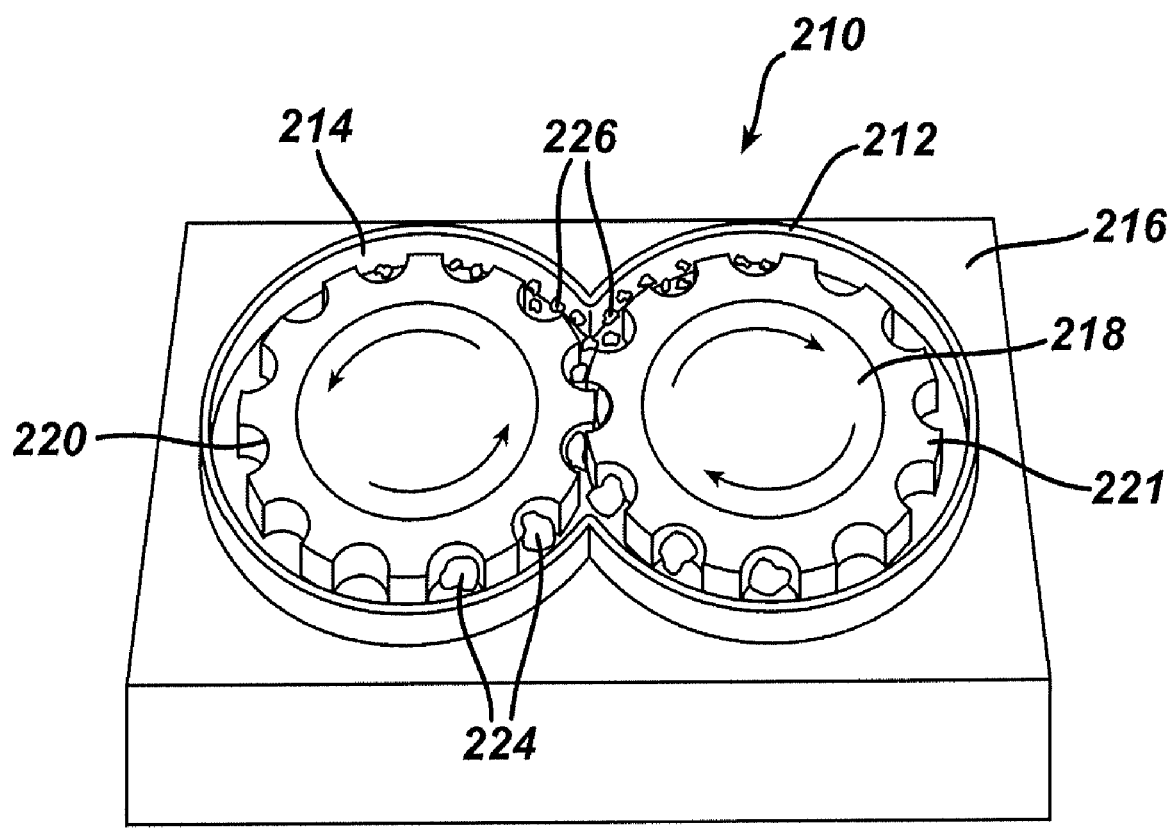
FIG. 5 is another perspective view of the tissue processing system of FIG. 4, showing the deposited tissue being ground by the system.

FIGS. 4-5 depict another exemplary tissue processing system (200). Tissue processing system (200) of this example comprises a tissue dispenser (250), a tissue processing tray (210), and a plurality of tissue grinders (218). Like tissue processing system (100) described above, and as will be described in greater detail below, tissue processing system (200) is operable to process tissue cores (222) by grinding the tissue cores (222) into minced tissue (226). This minced tissue (226) may then be incorporated into a fibrin matrix or scaffold, or into a variety of other types of mixtures with any one or more medical fluid components as referred to herein, in accordance with the teachings of any of the patents or patent publications cited herein, or in any other suitable fashion. The resulting matrix, scaffold, or other type of mixture may then be administered to a patient (e.g., the person from whom tissue cores (222) were originally obtained, etc.) for therapeutic purposes and/or for other purposes, in accordance with the teachings of any of the patents or patent publications cited herein, or in any other suitable fashion.

Tissue dispenser (250) is operable to obtain one or more tissue cores (222) from a patient and deposit such tissue cores (222) in tissue processing tray (210). Tissue dispenser (250) of the present example comprises a tissue reservoir (252) and a tissue coring needle (254). Tissue dispenser (250) further comprises a pump feature such as a plunger (not shown), which may be used to urge a tissue material (260) out of tissue dispenser (250) as a core (222) through needle (254). Tissue reservoir (252) comprises a generally cylindrical chamber configured to hold tissue material (260) and/or other biological material(s) therein. However, any suitable shape for tissue reservoir (252) may be used. Tissue reservoir (252) may be constructed of a plastic, metal, or any other suitable material or combination of materials. Tissue reservoir (252) is in fluid communication with needle (254). However, tissue reservoir (252) may be configured to be in fluid communication with needle (254) on a selective basis. For example, needle (254) and/or reservoir (252) may have a switch, valve, or other suitable actuation feature to enable a user to separate material held in tissue reservoir (252) from needle (254). The actuation feature may then be engaged to permit tissue reservoir (252) and needle (254) to be in fluid communication.

Needle (254) has a first end (258) and a second end (256). First end (258) connects to tissue reservoir (252) and second end (256) defines an opening through which tissue material (260) may be ejected from needle (254) as a tissue core (222). Second end (256) comprises a generally cylindrical opening. However, any suitable shape for the opening may be used. For example, the opening of second end (256) may be a slotted opening, a serrated opening, or any other suitable variation. Needle (254) may be formed of stainless steel material, plastic, and/or any other suitable material(s). Of course, tissue dispenser (250) may take a variety of other forms. For instance, tissue dispenser (250) may alternatively be configured similar to a conventional biopsy device having a needle with a closed distal end and a side aperture, with a cutter being movably positioned within the needle to sever tissue protruding through the side aperture. Other suitable forms that a tissue dispenser (250) may take will be apparent to those of ordinary skill in the art in view of the teachings herein. In the present example, tissue dispenser (250) obtains tissue material (260) from a patient's thigh muscle, though it should be understood that tissue material (260) may come from any other suitable source. Furthermore, it should be understood that the same device that obtains tissue material (260) need not necessarily be the same device that deposits tissue cores (222) in tissue processing tray (210).

Tissue processing tray (210) of the present example comprises a tray base (216) and tray walls (212). Tray base (216) is generally flat and rectangular in shape, though it should be understood that any other suitable shape(s) may be used. For example, a circular or elliptical shape may be used for tray base (216). Tray base (216) and tray walls (212) may be integrally formed as one piece or may be separately formed and later connected by, for example, welding, gluing, or any other suitable method. At least a portion of tray base (216) is configured to receive a plurality of tissue grinders (218). Tray base (216) is further configured to receive a tissue core (222) formed by tissue material (260) as it is ejected from tissue reservoir (252) of tissue dispenser (250). Tray base (216) may comprise a non-stick material (e.g., a coating of polytetrafluoroethylene (PTFE), etc.).

Tray walls (212) are configured to encompass tissue grinders (218). Thus, as shown in FIG. 4, since tissue grinder (218) is circular, tray walls (212) each have a partial circular shape, such that tray walls (212) together define a figure eight or peanut shape. Of course, any other suitable shape(s) for tray walls (212) may be used. In the present example, tray walls (212) form an enclosure around tissue grinders (218) that is only slightly larger than the overall size presented by tissue grinders (218), as shown in FIG. 4. Alternatively, tray walls (212) may be configured to form an enclosure that is substantially larger than the combined size of tissue grinders (218). Tray walls (212) of the present example also extend upwards perpendicular to tray base (216), to a height sufficiently high so as to prevent tissue core (222) from escaping tissue processing tray (210) as tissue core (222) is being processed as will be described in further detail below.

Tray walls (212) present an interior tray wall surface (214). In the illustrated version, tray wall surface (214) is generally smooth and is configured to allow smooth motion of plurality of tissue grinders (218). Tray wall surface (214) may comprise a generally non-stick material (e.g., a coating of polytetrafluoroethylene (PTFE), etc.), so as to substantially prevent tissue core (222) from sticking to tray wall surface (214).

Tissue grinders (218) are seated within tray walls (212) and are further seated upon tray base (216). Each tissue grinder (218) has a generally round gear-like shape. However, any other suitable shape(s) for each tissue grinder (218) may be used. Each tissue grinder (218) further comprises a respective tissue interface wall (220). Tissue interface walls (220) comprise a series of interlocking teeth (221) that extend radially outwardly from their respective tissue grinder (218) and that are operable to allow tissue grinders (218) to engage one another through the meshing of teeth (221). However, any other suitable configuration of tissue interface walls (220) may be used to provide an interface between tissue grinders (218). In the present example, meshing teeth (221) of tissue interface walls (220) are configured to dice and mince tissue core (222) as tissue grinders (218) are rotated. For example, the edges of teeth (221) may comprise a sharp edge or a serrated edge operable to dice and mince tissue. When tissue grinders (218) rotate (e.g., rotating in opposite directions) as shown in FIG. 5, teeth (2210) mesh and selectively interlock with each other to dice, mince, and mix tissue core (222) into minced tissue (226).

In some other versions, a first set of teeth of tissue grinders (218) is configured to dice tissue core (222) while a second set of teeth of tissue grinders (218) is configured to mince tissue. The first set of teeth of tissue grinders (218) may be located along a first portion of the outer perimeter of each tissue grinder (218) while the second set of teeth of tissue grinders (218) may be located along a different portion of the outer perimeter of each tissue grinder (218). Alternatively, each tissue grinder (218) may comprise a series of alternating first and second set of teeth for dicing and mincing, respectively, or any other suitable variations as will be apparent to those of ordinary skill in the art in view of the teachings herein.

Each tissue grinder (218) may have a respective shaft (not shown) coupled at the center of tissue grinder (218) and further extending through tray base (216). Rotary motion of the shafts is then communicated to tissue grinders (218). As a result, the shafts may be rotated directly or indirectly to cause rotation of plurality of tissue grinders (218). By way of example only, such shafts may be rotationally driven by one or more electric motors, pneumatic motors, or any other suitable driving device within tray base (216). Such a motor or other tissue grinder (218) driving device may be selectively activated by a button, switch, or other feature provided by tray base (216). Alternatively, tissue grinders (218) may be rotated manually, in a manner similar to tissue grinder (118) described above (e.g., by a user directly contacting one or both tissue grinders (218) with their finger, etc.). As another merely illustrative example, tissue grinders (218) may be manually rotated by a crank or other type of manual rotary driver. It should also be understood that tissue grinders (218) are rotationally coupled with each other by meshing teeth (221), such that actively rotating just one tissue grinder (218) will cause the other tissue grinder (218) to rotate in the present example. Of course, tray base (216) may also include gearing and/or other mechanical features configured to provide simultaneous active rotation of both tissue grinders (218) in response to a single motor or other drive means being activated.

Generally, tissue processing system (200) depicted in FIGS. 4-5 may be operated to dice, mince, or mix tissue. For instance, in an exemplary use of tissue processing system (200), tissue material (260) is initially obtained from a patient using needle (254) of tissue dispenser (250). Tissue material (260) is then ejected into tissue processing tray (210) from tissue dispenser (250) through needle (254) as shown in FIG. 4. As tissue material (260) leaves needle (254), tissue material (260) forms a generally cylindrically shaped tissue core (222) placed in tissue processing tray (210) between each of plurality of tissue grinders (218). However tissue core (222) need not be cylindrically shaped. It should also be understood that tissue material (260) may be directly added to tissue processing tray (210) without the use of tissue dispenser (250). After adding a sufficient amount of tissue core (222) to tissue processing tray (210), a user then actuates at least one of tissue grinders (218), which causes each of plurality of tissue grinders (218) to rotate in opposite directions about respective axes. As tissue grinders (218) rotate, tissue grinders (218) continually engage and disengage each other through interlocking teeth (221). This meshing of teeth (221) draws tissue core (222) into meshed teeth (221), which dice, mince, and mix tissue core (222) to form minced tissue (226) as shown in FIG. 5.

As tissue grinders (218) rotate and interface with each other, tissue core (222) is located at the area where tissue grinders (218) interface, such that tissue core (220) diced, minced and mixed. In the present example, tissue grinders (218) still provide a slight gap to provide space for tissue core (222) as tissue core (222) is being diced, minced, and mixed, without simply crushing tissue core (222). As tissue core (222) is diced, minced, and mixed, tissue core (222) is constantly in motion such that portions of tissue core (222) that have already been diced, minced, or mixed move away from the area where tissue grinders (218) engage each other. Furthermore, tissue core (222) that has not been diced, minced, or mixed then moves into the area where tissue grinders (218) engage each other. After tissue core (222) is sufficiently diced, minced, and mixed, the resulting minced tissue (226) may be removed from tissue processing tray (210) in any suitable fashion, then subsequently processed and/or re-administered to the patient in accordance with the teachings herein and/or in accordance with the teachings in any patents and/or published patent applications cited herein. Of course, several tissue cores (222) may be introduced to tissue processing tray (210), serially and/or simultaneously, to produce a desired amount of minced tissue (226). To remove minced tissue (226) from processing tray (210), a user may simply lift and remove tissue grinders (218) from processing tray (210) and then scoop minced tissue (226) from processing tray (210). Of course, any suitable technique may be used to remove minced tissue (226) from processing tray (210).

In some other versions, tissue grinders (218) may be configured to dice tissue core (222) when tissue grinders (218) are rotated in one set of opposing directions to produce diced tissue (224); and to mince diced tissue (224) when tissue grinders (218) are rotated in another set of opposing directions to produce minced tissue (226). As another merely illustrative example, tissue grinders (218) may be configured to dice and mince tissue core (222) when tissue grinders (218) are rotated in one set of opposing directions to produce diced tissue (224) then minced tissue (226); and to mix diced tissue (224) and minced tissue (226) when tissue grinders (218) are rotated in another set of opposing directions.

As noted above, tray base (216) may include a button or other user input feature for selectively activating a motor to cause rotation of tissue grinders (218). It should also be understood that a plurality of actuation features may be provided. For example, one actuation feature may be configured to cause tissue grinders (218) to rotate in one direction thereby dicing and mincing tissue core (222). A different actuation feature may be configured to cause tissue grinders (218) to rotate in a different direction thereby mixing diced tissue (224) and minced tissue (226). It should also be understood that, during the process of dicing and mincing in various versions of tissue processing system (200), tissue core (222) and/or diced tissue (224) and/or minced tissue (226) may become mixed; and furthermore, that a user may add other suitable materials (e.g., fibrin, polymer, etc.) to tissue processing tray (210) to be diced, minced, and/or mixed with tissue core (222) and/or diced tissue (224) and/or minced tissue (226). Still other suitable features, components, configurations, functionalities, and operabilities that may be provided by tissue processing system (200) will be apparent to those of ordinary skill in the art in view of the teachings herein. Similarly, various other suitable ways in which tissue processing system (200) may be used will be apparent to those of ordinary skill in the art in view of the teachings herein.

Figure 6:
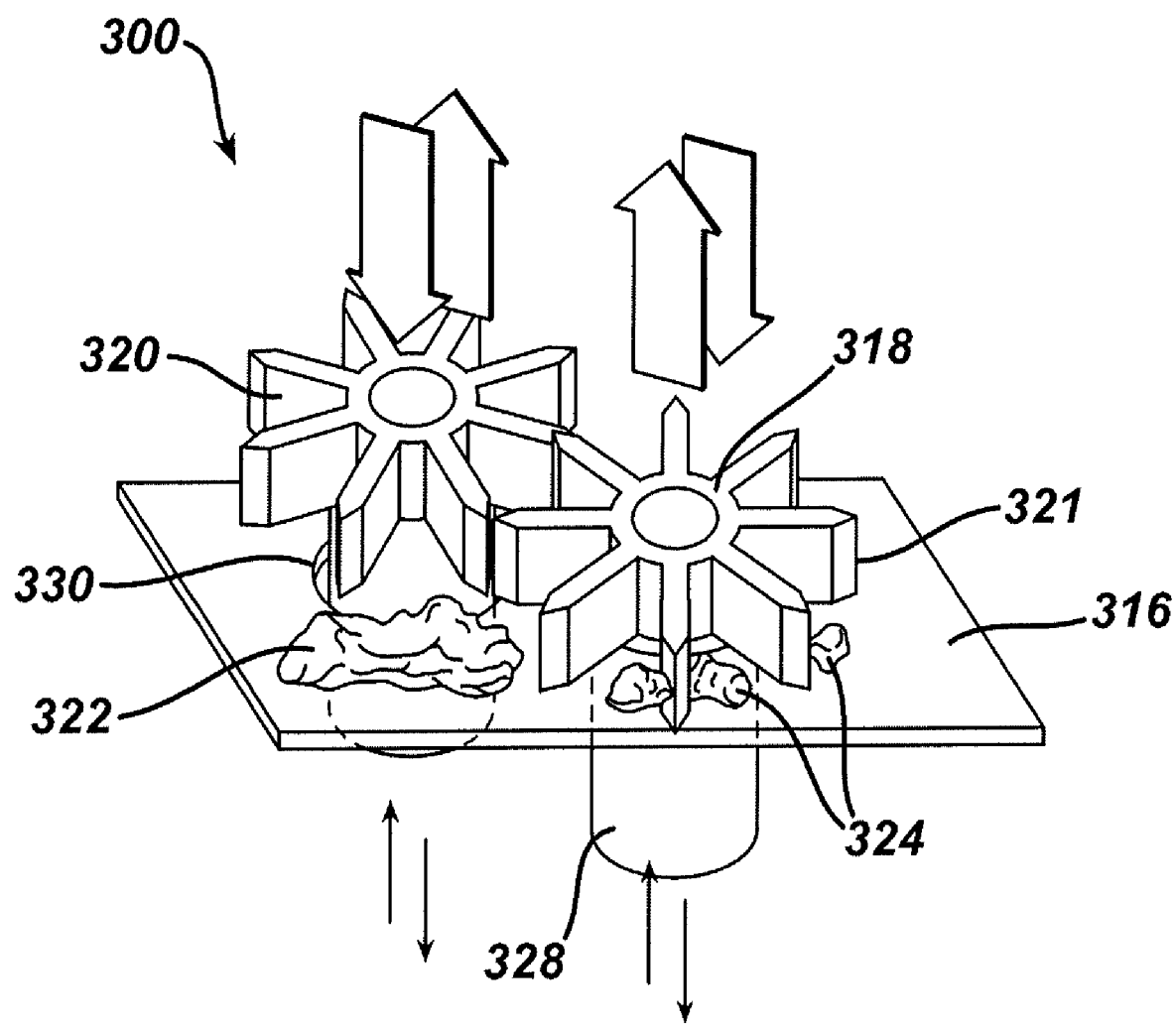
FIG. 6 is a perspective view of yet another exemplary alternative version of a tissue processing system, showing processors reciprocating to dice tissue.
Figure 7:
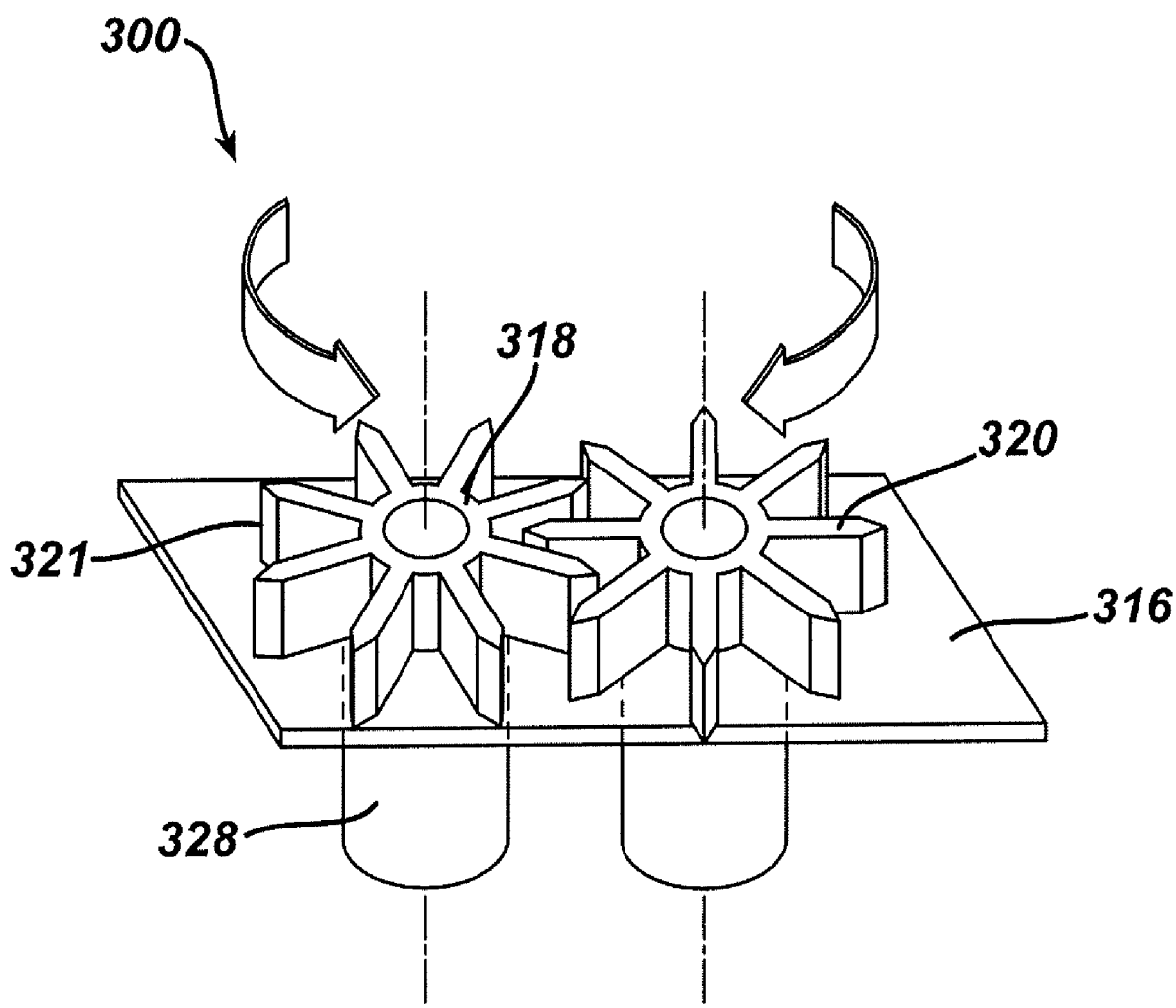
FIG. 7 is another perspective view of the tissue processing system of FIG. 6, showing the processors rotating to mince and mix the diced tissue.

C. Exemplary Tissue Processing Device with Dual Rotary and Reciprocating Grinders FIGS. 6-7 depict yet another exemplary tissue processing system (300). Tissue processing system (300) of this example comprises a tissue processing base (316), a plurality of tissue grinders (318), and a plurality of tissue grinder shafts (328). Like tissue processing systems (100, 200) described above, and as will be described in greater detail below, tissue processing system (300) is operable to dice and mince tissue cores (322). This minced tissue may then be incorporated into a fibrin matrix or scaffold, or into a variety of other types of mixtures with any one or more medical fluid components as referred to herein, in accordance with the teachings of any of the patents or patent publications cited herein, or in any other suitable fashion. The resulting matrix, scaffold, or other type of mixture may then be administered to a patient (e.g., the person from whom tissue cores (322) were originally obtained, etc.) for therapeutic purposes and/or for other purposes, in accordance with the teachings of any of the patents or patent publications cited herein, or in any other suitable fashion. While no tissue dispenser is shown in FIGS. 6-7, it should be understood that tissue processing system may receive tissue cores (322) from a tissue dispenser (150, 250) like those described above or from any other suitable type of device. It should also be understood that, like tissue processors (100, 200), tissue processing system (300) may process various types of tissue in various forms. In other words, it is not necessary in all versions for any tissue processor (100, 200, 300) described herein to receive tissue in a "core" type of form per se.

Tissue processing base (316) comprises a flat surface configured to receive a tissue core (322). Tissue processing base (316) further defines a pair of openings (330). Tissue grinder shafts (328) extend through openings (330). The upper contact surface of tissue processing base (316) is impact resistant, such that the surface is configured to withstand various motions of plurality of tissue grinders (318). Tissue processing base (316) may also include a non-stick material (e.g., a coating of polytetrafluoroethylene (PTFE), etc.) to prevent tissue core (322) from sticking to tissue processing base (316). In some versions, tissue processing base (316) may comprise a material and/or surface features configured to grip tissue core (322). It should also be understood that tissue processing base (316) may comprise alternating regions of non-stick material and non-slip material or any other suitable variations as will be apparent to one of ordinary skill in the art in view of the teachings herein. Furthermore, while not shown in FIGS. 6-7, it should be understood that tissue processing base (316) may further comprise side walls (not shown) that are configured to enclose tissue grinders (318) and that are further configured to prevent tissue core (322) from unintentionally exiting tissue processing base (316). By way of example only, such sidewalls may be configured similar to tray walls (212) described above.

Tissue grinders (318) of the present example each have a star-like shape, such that tissue grinders (318) are configured to interface with each other. In particular, tissue grinders (318) each comprise a plurality of tissue processing fins (320) extending radially outward from the center of each tissue grinder (318). Tissue processing fins (320) are configured to dice tissue core (322) and/or mix diced tissue with a fluid medium when tissue grinders (318) are moved in an up and down motion as shown in FIG. 6 and/or when tissue grinders (318) are rotated as shown in FIG. 7. In the present example, the width of each tissue processing fin (320) is substantially uniform along its height. In some versions, tissue processing fins (320) have a width that tapers along the height of each tissue processing fin (320), such that each tissue processing fin (320) terminates in a sharp edge at the bottom of tissue processing fin (320) to facilitate dicing of tissue core (322). Each tissue processing fin (320) of the present example also has a sharp edge (321) at its radially outermost point. Sharp edges (321) are configured to mince tissue core (322) that passes between tissue grinders (318) as tissue grinders (318) are rotated and mesh with each other.

Each tissue grinder (318) is connected to a respective tissue grinder shaft (328). Vertical reciprocating motion of tissue grinder shafts (328) is communicated to tissue grinders (318). Thus, tissue grinders (318) may be translated up and down as shown in FIG. 6 by reciprocating tissue grinder shafts (328) up and down. By way of example only, tissue grinder shafts (328) may be linearly driven by one or more solenoids, pneumatic actuators, or ant other suitable driving device. Such a solenoid, pneumatic actuator, etc. may be selectively activated by a button, switch, or other feature provided by tissue processing system (300). Alternatively, tissue grinder shafts (328) may be reciprocated manually (e.g., using a crank and camshaft, etc.). Of course, tissue processing system (300) may also include gearing and/or other mechanical features configured to provide simultaneous reciprocation of both tissue grinder shafts (328) in response to a solenoid or other drive means being activated. In the present example, tissue processing system (300) is configured such that tissue grinder shafts (328) reciprocate in an opposing manner (e.g., such that one tissue grinder shaft (328) translates upwardly while the other tissue grinder shaft (328) translates downwardly and vice-versa, etc.). In some other versions, tissue processing system (300) is configured such that tissue grinder shafts (328) reciprocate in unison (e.g., such that both tissue grinder shafts (328) translate upwardly simultaneously and downwardly simultaneously). In still other versions, tissue processing system (300) is configured such that one tissue grinder shaft (328) reciprocates while the other tissue grinder shaft (328) does not reciprocate.

In addition, rotary motion of tissue grinder shafts (328) is communicated to tissue grinders (318). Thus, tissue grinder shafts (328) may be rotated to cause rotation of tissue grinders (318) as shown in FIG. 7. By way of example only, tissue grinder shafts (328) may be rotationally driven by one or more electric motors, pneumatic motors, or any other suitable driving device. Such a motor or other tissue grinder shaft (328) driving device may be selectively activated by a button, switch, or other feature provided by tissue processing system (300). Alternatively, tissue grinder shafts (328) may be rotated manually (e.g., by a user directly contacting one or both tissue grinders (318) with their finger, etc.). As another merely illustrative example, tissue grinder shafts (328) may be manually rotated by a crank, rotational ring, or other type of manual rotary driver. It should also be understood that tissue grinders (318) are rotationally coupled with each other by meshing fins (320), such that actively rotating just one tissue grinder (318) will cause the other tissue grinder (318) to rotate in the present example. Of course, tissue processing system (300) may also include gearing and/or other mechanical features configured to provide simultaneous active rotation of both tissue grinders (318) in response to a single motor or other drive means being activated.

Various suitable ways in which tissue grinder shafts (328) may be reciprocated by a solenoid or other device then rotated by a motor or other device will be apparent to those of ordinary skill in the art in view of the teachings herein. In other words, various components and features that may be used to provide an interface between one or more solenoids and tissue grinder shafts (328), as well as various components and features that may be used to provide an interface between one or more motors and tissue grinder shafts (328), will be apparent to those of ordinary skill in the art in view of the teachings herein. Furthermore, tissue grinder shafts (328) may comprise a locking feature configured to selectively lock either rotation of tissue grinder shafts (328) or reciprocation of tissue grinder shafts (328). Such a locking feature may comprise a switch or other component to engage the locking feature. Thus, the user can select whether tissue grinder shafts (328) rotate or reciprocate to the exclusion of the other type of motion. It should also be understood that tissue processing system (300) may be configured to simultaneously rotate tissue grinder shafts (328) and reciprocate tissue grinder shafts (328), such that both tissue grinders (318) rotate as they move up and down. In such versions, the reciprocation of tissue grinder shafts (328) may be synchronized or non-synchronized. For instance, when a first tissue grinder (318) is in an "up" position while a second tissue grinder (318) is in a "down" position, rotation of one or both tissue grinders (318) and/or vertical movement of one or both tissue grinders (318) may provide mixing of a fluid/solid medium (e.g., mixture of tissue and fibrin or some other scaffold material, etc.). When the first tissue grinder (318) is in a "down" position while the second tissue grinder (318) is also in the "down" position (e.g., such that tissue grinder shafts (328) are not reciprocating), rotation of both tissue grinders (318) may provide dicing of the solid part (e.g., tissue, etc.) of the fluid/solid medium.

Generally, tissue processing system (300) as shown in FIGS. 6-7 may be operated to dice, mince, or mix tissue. For instance, in an exemplary use of tissue processing system (300), tissue core (322) is initially obtained from a patient. Tissue core (322) is then deposited on tissue processing base (316). To the extent that a locking feature is present, the user may then actuate the locking feature to select tissue grinder shafts (328) to move in only an up and down motion. The user then activates one or more solenoids or other actuators to cause tissue grinder shafts (328) to reciprocate, which in turn causes up and down motion of tissue grinders (318) as shown in FIG. 6. As tissue grinders (318) move up and down, tissue grinders (318) dice tissue core (322). After the user decides that tissue core (322) is sufficiently diced and a sufficient amount of diced tissue (324) is produced, the user may then engage the locking feature (if one is present) to only allow tissue grinder shafts (328) to rotate rather than reciprocate. The user then activate one or more motors or other devices to cause tissue grinder shafts (328) to rotate, which in turn causes rotation of tissue grinders (318) as shown in FIG. 7. As tissue grinders (318) rotate, tissue grinders (318) continually engage and disengage each other through interlocking fins (320). This meshing of fins (320) draws diced tissue (324) into meshed fins (320), which mince and mix diced tissue (324) to form minced tissue (not shown). After tissue core (322) is sufficiently diced, minced, and mixed, the resulting minced tissue may be removed from tissue processing base (316) in any suitable fashion, then subsequently processed and/or re-administered to the patient in accordance with the teachings herein and/or in accordance with the teachings in any patents and/or published patent applications cited herein. Of course, several tissue cores (322) may be introduced to tissue processing base (316), serially and/or simultaneously, to produce a desired amount of minced tissue. To remove minced tissue from processing base (316), a user may simply open a hinged hood or other component that holds tissue grinders (318) to move tissue grinders (318) away from processing base (316) and then scoop the minced tissue from processing base (316). Of course, any suitable technique may be used to remove minced tissue from processing base (316).

In some other versions, the dicing and mincing of tissue core (322) may be combined in one stage. For example, rather than an exclusively up and down motion in one stage and an exclusively rotational motion in another stage, the up and down motion and the rotational motion of tissue grinders (318) may be provided simultaneously. In other words, with a single actuation, the up and down movement and rotational movement may occur simultaneously resulting in a helical twisting motion of each fin (320) to dice and mince tissue core (322) at once. In some other versions, the motion of tissue grinders (318) may be combined by serially performing the motions. In other words, with a single actuation, tissue grinders (318) may be moved up and down directly followed by a rotational motion. Still other suitable features, components, configurations, functionalities, and operabilities that may be provided by tissue processing system (300) will be apparent to those of ordinary skill in the art in view of the teachings herein. Similarly, various other suitable ways in which tissue processing system (300) may be used will be apparent to those of ordinary skill in the art in view of the teachings herein.

III. Exemplary Fistula Plug Preparation System

FIGS. 8-13 depict an exemplary fistula plug preparation system (400). In the present example, fistula plug preparation system (400) is operable to provide a plug for use in surgery to treat a fistula or other type of anatomical defect, etc. For instance, the plug may be sized and configured for delivery into a variety of fistula tracts. The plug generally comprises a scaffold material (404) formed into a narrow cylindrical shape that is configured for insertion into a fistula with a cell matrix. Scaffold material (404) may comprise a biocompatible material that may be formed from a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, polyhydroxybutyrate (PHB), poly(hyaluronic acid), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.), and/or any other suitable material or combination of materials. It should also be understood that scaffold material (404) may include any one or more of the various medical fluid components referred to herein. Other suitable materials will be apparent to those of ordinary skill in the art in view of the teachings herein.

As will be described in greater detail below, a plug formed of scaffold material (404) may be inserted into a fistula by a catheter (412), and may be flushed with a cell matrix to therapeutically address the fistula. Such a cell matrix may be formed at least in part by tissue that was harvested from the same patient that has the fistula (and/or tissue harvested from some other source or sources). For instance, at least some of the cells in the cell matrix may be isolated or derived in part from such harvested tissue. The cells may include, for example, genetically engineered cells, precursor cells, progenitor cells, precursor cells, stem cells, bone marrow cells, umbilical cord blood cells, angioblasts, endothelial cells, osteoblasts, smooth muscle cells, kidney cells, fibroblasts, myofibroblasts, cardiovascular cells, neural cells, neural precursor cells, amniotic cells and post-partum placental cells, any other type of cells referred to herein, and/or any other suitable types of cells, including combinations of different kinds of cells. Such harvested tissue may have been minced using any of the tissue processing systems (100, 200, 300) described herein and/or may have been processed in any other suitable fashion before being introduced to scaffold material (404). While the cell matrix is introduced to a plug formed by scaffold material (404) after the plug has been inserted in a fistula or as the plug is being inserted in a fistula in the present example, it should be understood that the cell matrix may alternatively be introduced to scaffold material (404) before or during the process in which scaffold material (404) is formed into a plug or at any other suitable time.

Figure 8:
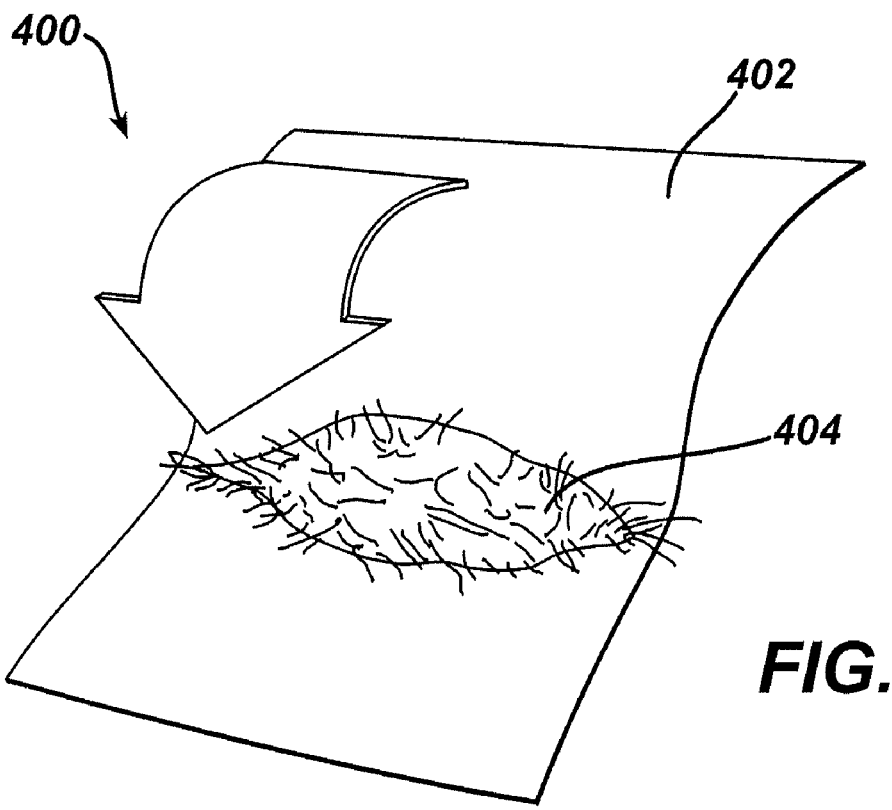
FIG. 8 is a perspective view of an exemplary alternative version of a tissue processing system, shown in a first stage of an exemplary process.
Figure 9:
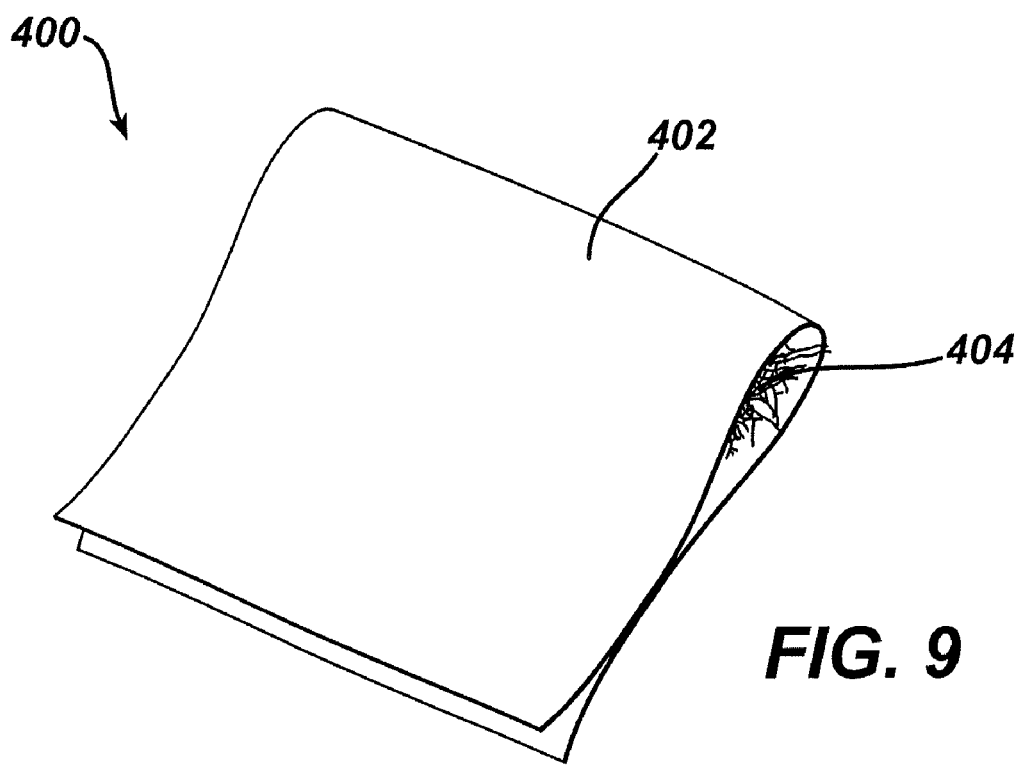
FIG. 9 is another perspective view of the tissue processing system of FIG. 8, shown in a second stage of the process.

Fistula plug preparation system (400) of this example comprises a wrapper (402), a slotted plate (416), a forming device (406), a plunger (408), and a catheter (412). Wrapper (402) generally comprises a thin foldable sheet operable to receive scaffold material (404). Wrapper (402) may be formed at least in part of a generally non-stick material or materials (e.g., silicone, ultra high molecular weight polyethylene, a coating of polytetrafluoroethylene (PTFE), etc.) that is configured to prevent scaffold material (404) from sticking to wrapper (402), even if wrapper (402) is folded over itself with scaffold material (404) contained therein. Wrapper (402) is configured to transition from a flat position as shown in FIG. 8 to a folded position as shown in FIG. 9. However, any suitable position for wrapper (402) may be used to enclose scaffold material (404).

Figure 10:
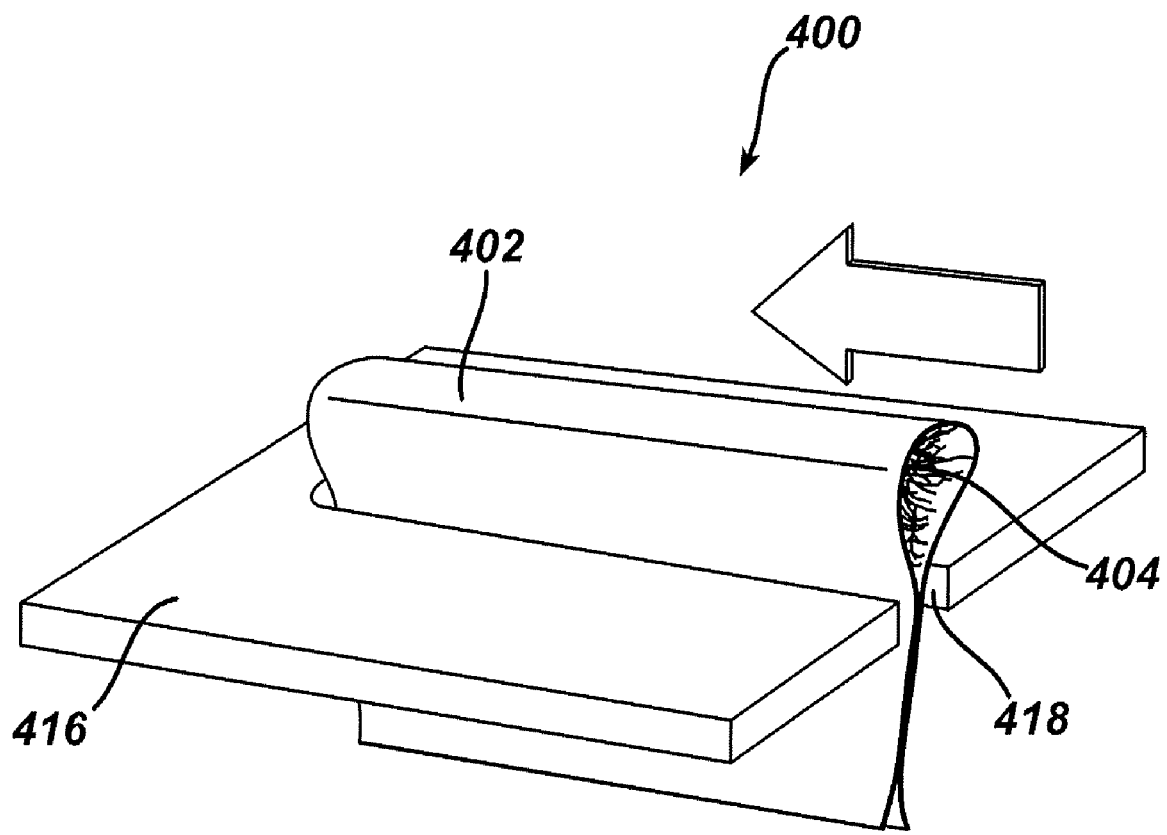
FIG. 10 is another perspective view of the tissue processing system of FIG. 8, shown in a third stage of the process.

Slotted plate (416) comprises a generally flat and rectangular plate. However, it should be understood that slotted plate (416) may have any other suitable shape, configuration, or size. Slotted plate (416) defines a slot (418) extending through slotted plate (416). Slot (418) extends along almost the entire length of slotted plate (416) such that a portion of slotted plate (416) still connects what would otherwise be two separate portions of slotted plate (416). As shown in FIG. 10, folded wrapper (402) containing scaffold material (404) may be inserted into slot (418) of slotted plate (416), such that the length of wrapper (402) containing scaffold material (404) may extend for at least part of the length of slot (418). Furthermore, slot (418) is sufficiently narrow so as to prevent scaffold material (404) from inadvertently falling out of wrapper (402) thought slot (418). At this stage, wrapper (402) may be pulled downwardly relative to slotted plate (416). It should be understood that such pulling may allow wrapper (402) to compress scaffold material (404) by bearing against slotted plate (416). In addition or in the alternative, opposite ends of wrapper (402) may be alternatingly pulled down in a rocking fashion to roll scaffold material (404) within wrapper (402).

Figure 11:
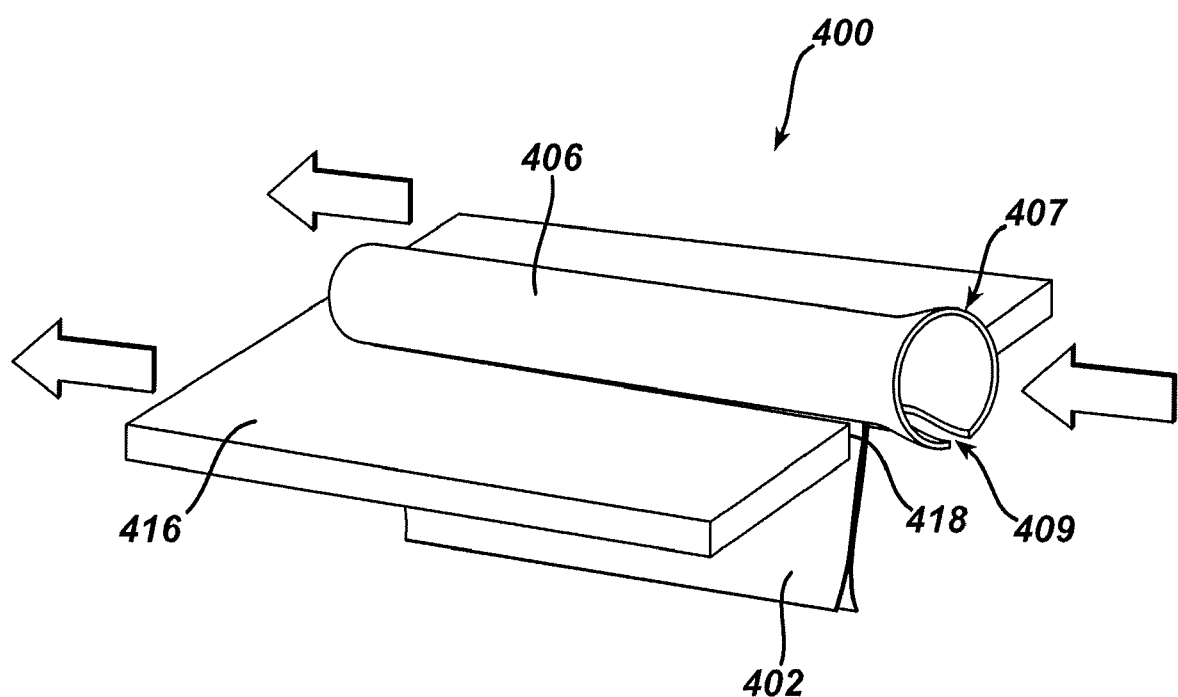
FIG. 11 is another perspective view of the tissue processing system of FIG. 8, shown in a fourth stage of the process.

As shown in FIG. 11, forming device (406) comprises a cylindrical tube having a flared end (407). While wrapper (402) is substantially flexible in the present example, forming device (406) is substantially rigid (e.g., formed of steel, rigid plastic, etc.) in the present example. Forming device (406) further comprises a slot (409) extending along the full length of forming device (406). Slot (409) is configured to allow wrapper (402) containing scaffold material (404) to fit within forming device (406) such that at least a portion of wrapper (402) extends though slot (409) of forming device (406) in addition to extending through slot (418) of slotted plate (416). Flared end (407) of forming device (406) is configured to allow easy insertion of wrapper (402) containing scaffold material (404) into forming device (406). Furthermore, the inner diameter of forming device (406) may be smaller than the outer diameter of wrapper (402) containing scaffold material (404), such that once forming device (406) is placed over wrapper (402) containing scaffold material (404), wrapper (402) containing scaffold material (404) is compressed to form a generally cylindrical shape. Of course, forming device (406) may be any other suitable shape, and may be configured to form scaffold material (404) into any other suitable shape.

Figure 12:
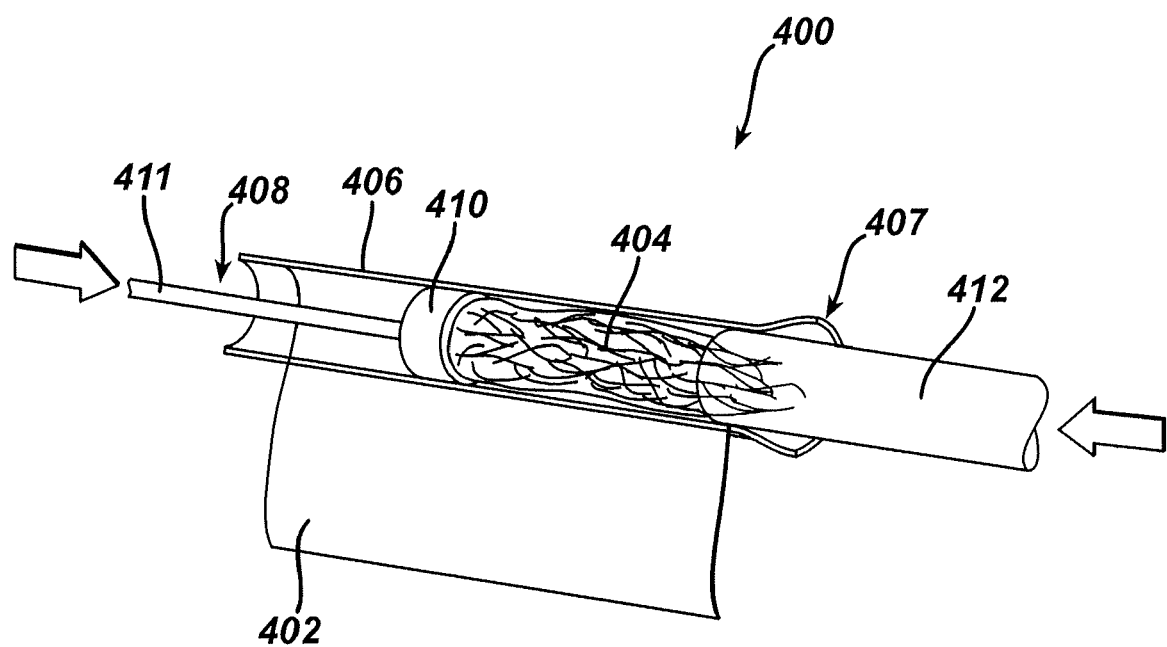
FIG. 12 is another perspective view of the tissue processing system of FIG. 8, shown in a fifth stage of a process.
Figure 13:
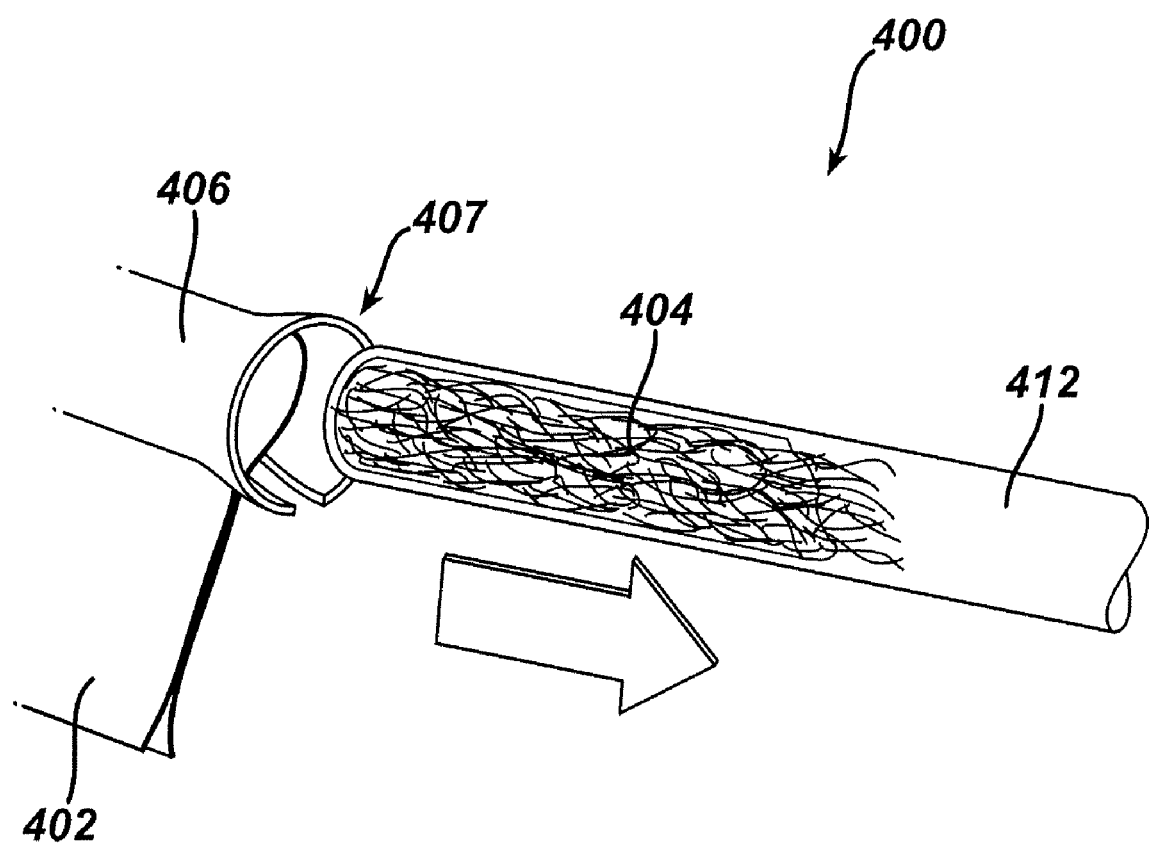
FIG. 13 is another perspective view of the tissue processing system of FIG. 8, shown in a sixth stage of the process.

As shown in FIGS. 12-13, scaffold material (404) that has been formed into a cylindrical shape may be inserted into catheter (412). Catheter (412) of the present example has a generally cylindrical shape, though it should be understood that any other suitable shape may be used. Catheter (412) may be positioned at flared end (407) of forming device (406) for receipt of scaffold material (404). Removal plunger (408), which comprises an elongate shaft (411) having a piston-like head (410), may then be inserted into the opposite end of forming device (406) to urge scaffold material (404) out of forming device (406) and out of wrapper (402), into catheter (412). Thus, removal plunger (408) may be used to push scaffold material (404) into catheter (412) from forming device (406). Once scaffold material (404) is removed from forming device (406) and placed in catheter (412), catheter (412) with scaffold material (404) may be removed and used immediately or stored for later use.

When catheter (412) is ready for use to deploy scaffold material (404), catheter (412) may be inserted in a fistula tract and then scaffold material (404) may be ejected as a plug into the fistula. To the extent that a cell matrix had not yet been introduced to scaffold material (404) at this stage, the cell matrix or slurry may be communicated through catheter (412) or in some other way to impregnate scaffold material (404) as catheter (412) is being withdrawn from the fistula to leave impregnated scaffold material (404) within the fistula. The impregnated scaffold material (404) may thus be deployed within the fistula in a manner similar to that by which a self-expanding stent is deployed. Of course, scaffold material (404) may alternatively be deployed in any other suitable fashion. Still other suitable features, components, configurations, functionalities, and operabilities that may be provided by fistula plug preparation system (400) will be apparent to those of ordinary skill in the art in view of the teachings herein. Similarly, various other suitable ways in which fistula plug preparation system (400) may be used will be apparent to those of ordinary skill in the art in view of the teachings herein.

IV. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for processing tissue by using a tissue processor, wherein the tissue processor comprises a plurality of rotary members and a tray, wherein the plurality of rotary members mesh with each other, wherein each of the rotary members defines a respective axis, wherein the tray is configured to receive tissue, the method comprising:
   (a) placing the tissue in the tray of the tissue processor;
   (b) actuating the rotary members, wherein the act of actuating the rotary members comprises:
      (i) rotating the rotary members simultaneously, and
      (ii) moving the rotary members linearly along their respective axes, and
      (iii) processing the tissue by grinding the tissue within meshing regions of the simultaneously rotating rotary members; and
   (c) removing the ground tissue from the tissue processor.

2. The method of claim 1, wherein the act of rotating the rotary members simultaneously comprises actively rotating a first one of the rotary members, wherein the first one of the rotary members rotatingly drives at least a second one of the rotary members to provide simultaneous rotation of the rotary members.

3. The method of claim 1, wherein the act of processing the tissue comprises one or more of dicing the tissue, mincing the tissue, or mixing the tissue.

4. The method of claim 1, wherein the act of moving the rotary members linearly along their respective axes further comprises:
   (i) moving a first one of the rotary members upwardly along the axis of the first one of the rotary members while simultaneously moving a second one of the rotary members downwardly along the axis of the second one of the rotary members, then
   (ii) moving the first one of the rotary members downwardly along the axis of the first one of the rotary members while simultaneously moving the second one of the rotary members upwardly along the axis of the second one of the rotary members.

5. The method of claim 1, wherein the rotary members each have a respective set of outwardly extending fins.

6. The method of claim 1, wherein each rotary member is secured to a respective shaft.

7. The method of claim 6, wherein each shaft passes through the tray of the tissue processor.

* * * * *